(12) United States Patent
Goldman et al.

(10) Patent No.: US 6,437,222 B1
(45) Date of Patent: Aug. 20, 2002

(54) REDUCED PIGMENT GENE OF CARROT AND ITS USE

(75) Inventors: Irwin L. Goldman, Madison; D. Nicholas Breitbach, Middleton, both of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/136,913

(22) Filed: Aug. 20, 1998

(51) Int. Cl.$^7$ .............................. A01H 5/00; A01H 5/10; A01H 5/06; C12N 5/04
(52) U.S. Cl. .................. 800/298; 800/266; 800/260; 800/268; 435/410
(58) Field of Search ................................ 800/266, 260, 800/298; 435/410

(56) References Cited

PUBLICATIONS

Buishand et al. Euphytica. vol. 28, pp. 611–632, 1979.*
Bubicz et al. Przemysl Fermentacyjny i Owocowo–Warzywny. vol. 34, pp. 20–21, 1990.*
Hemeda et al. Journal of Food Science. vol. 56, pp. 68–71, 1991.*
Goldman et al. The Journal of Heredity. vol. 87, pp. 380–382, 1996.*
Warman et al. Agriculture, Ecosystems and Environment. vol. 61, pp. 155–162, 1997.*
Zelenin. Voprosy Pitaniya. No. 4, pp. 74–75, 1992.*
Goldman et al. The Journal of Heredity, vol. 87, pp. 380–382, 1996.*
http://www.hort.wise.edu/Goldman/lab/carrot.htm, 2001.*

* cited by examiner

Primary Examiner—Amy J. Nelson
Assistant Examiner—Anne Kubelik
(74) Attorney, Agent, or Firm—Rothwell, Figg, Ernst & Manbeck

(57) ABSTRACT

This invention relates to a carrot plant having Vitamin E biosynthesis, a recessive gene for reduced pigment designated rp, a carrot inbred line with Vitamin E biosynthesis. The carrot plant contains at least 0.01 mg α-tocopherol per 100 grams of fresh weight of the carrot root. The present invention also relates to a method for producing $F_1$ hybrid carrot root. The method includes crossing a first parent carrot plant with a second parent carrot plant and harvesting the resultant $F_1$ hybrid carrot root.

25 Claims, No Drawings

REDUCED PIGMENT GENE OF CARROT AND ITS USE

The present invention relates to a *Daucus carota* reduced pigment gene, a carrot seed, a carrot plant, a carrot inbred and a method of producing carrot hybrids. The reduced pigment gene of the present invention can be incorporated into various Daucus genetic backgrounds. The present invention also relates to a carrot root having an increased level of α-tocopherol.

BACKGROUND OF THE INVENTION

Carrot (*Daucus carota* L.) is a biennial plant that belongs to the parsley family. Carrot roots are commonly-known as a good source of Vitamin A. In particular, it has been estimated that carrots contribute approximately 14% of the total Vitamin A to the human diet in the United States (Senti, F. R., and R. L. Rizek, 1975, Nutrient Levels in Horticultural Crops. Hort.Science. 10:243–246). Vitamin A content is related to the pigmentation in the carrot roots. In particular, carrot roots contain β-carotene which animals convert into provitamin A. Beta carotene is also responsible for the orange color of carrot roots. Carrot pigmentation is present in carrots in many different forms. Carrot roots can exhibit several colors including white, yellow, orange, red and purple (Banga, 0., 1964, Origin and Distribution of the Western Cultivated Carrot. *Genetica Agrafia*. 17:357–370). Of these colors, purple pigmentation is due to the presence of anthocyanins whereas yellow, orange and red pigmentation are due to carotenoids. The primary carotenoids in orange carrot tissue are α and β-carotene (Laferriere, L., and W. H. Gabelman, 1968, Inheritance of Color, Total Carotenoids, Alpha-carotene, and Beta-carotene in Carrots, *Daucus carota* L., Proc. Amer. Soc. Hort. Sci. 93:408–418).

Carrot cultivars are often separated into several categories for market use. These include 1) fresh market, 2) cut and peel, and 3) processing. Fresh market carrots are typically known as Imperator types and have long, straight, thin roots. They are also known as cello or bunching carrots because they are sold bunched in cello bags in the market. Cut and peel carrots refer to the "baby" carrot now seen in markets throughout the world. These carrots have roots that are similar in type to the fresh market carrot, however, they have been cut into small sections for market. Processing carrots are large, often tapered, bulky roots used for canning, freezing, and other processed carrot products. Cultivars of processed carrot and fresh market carrot are developed and maintained in separate breeding programs.

Although the beta-carotene present in commonly-known carrots may be converted into Vitamin A in the body, sufficient levels of other nutrients must be obtained from sources other than carrots. For example, the presence of α-tocopherol has not been recorded in any carrot inbred, hybrid, or openpollinated cultivar. Furthermore, because α-tocopherol is usually associated with the oil fraction of plant extracts, (while carrots are consumed for their high moisture content and high fiber root) carrot inbred lines, hybrids, or open-pollinated cultivars have not been associated with this vitamin. Alpha tocopherol (Vitamin E) cannot be synthesized by the body. Alpha tocopherol is important in the body as a vitamin. Beyond its importance as a vitamin, α-tocopherol also possesses antioxidant activity. More specifically, α tocopherol along with other members of the Vitamin E family, namely, β, γ, and δ tocopherol and their corresponding unsaturated derivatives α, β, γ and δ tocotrienol, are primarily used by the body as antioxidants. Nevertheless, the average U.S. citizen consumes less than the U.S. Recommended Daily Allowance of 30 International Units of Vitamin E. Biosynthetic pathway for carotenoids (left column) and tocopherols (right column) are shown in Table 1 below:

TABLE 1

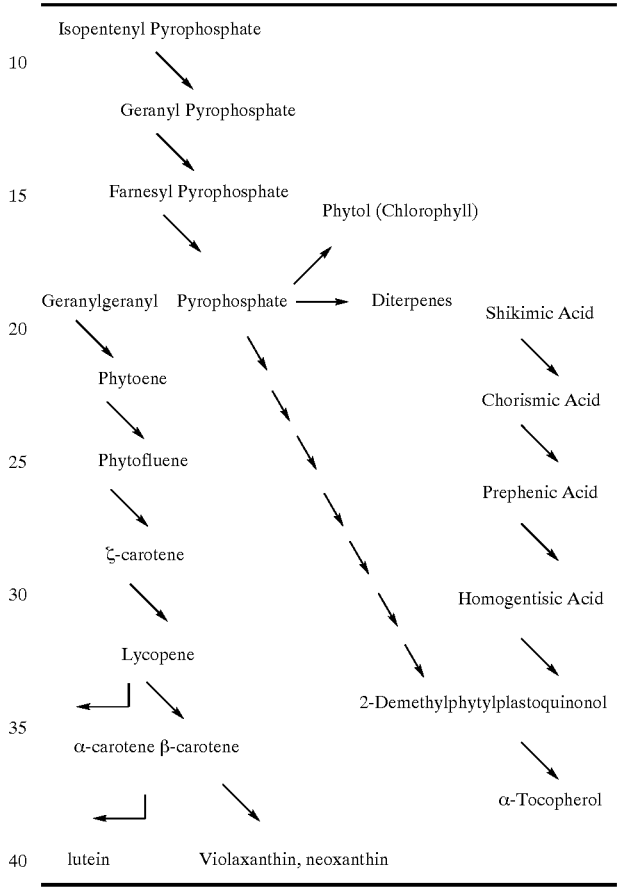

Biosynthesis of carotenoids and tocopherols is connected through the common intermediate geranylgeranyl pyrophosphate (GGPP), Norris et al., 1995, Plant Cell, 7:2139–2149.

Although some vegetables synthesize both α-tocopherol and β-carotene, these vegetables are primarily seed-producing plants such as maize and some seed oil plants. It would be desirable to have a new carrot that synthesizes α tocopherol (Vitamin E). Moreover, it would be desirable to have a carrot inbred line with α tocopherol synthesis in its root.

SUMMARY OF THE INVENTION

The present invention relates to a Daucus seed, a Daucus plant, a Daucus variety, a Daucus hybrid and a method for producing a Daucus plant.

More specifically, the invention relates to a carrot root having a mutant reduced pigment gene designed rp. The present invention is directed to a carrot root with a total α-tocopherol content between about 0.01 mg per 100 grams of fresh weight of the carrot root and about 0.40 mg per 100 grams of fresh weight of the carrot root. The present invention is also directed to an $F_1$ hybrid carrot plant having a total α-tocopherol content greater than about 0.01 mg per 100 grams of fresh weight of the carrot root. The present invention further relates to a method of producing the disclosed carrot plants and seeds by crossing a reduced pigment plant of the instant invention with another carrot plant. The invention also relates to the transfer of the genetic reduced pigment into other genetic backgrounds.

It is an object of this invention to provide a carrot that synthesizes α-tocopherol in its root. Generally, the carrot inbred line of the present invention provides for α-tocopherol biosynthesis in the root. The carrot seed of the present invention contains a recessive gene, designated rp, for a reduced pigment phenotype. The present invention is also directed to a reduced pigment carrot plant produced from growing the carrot seed. The carrot plant has an increased level of α-tocopherol. The α-tocopherol level of the carrot plant is at least 0.01 mg per 100 grams of fresh weight of the carrot. In general, a method of the present invention is for producing $F_1$ hybrid carrots. This method includes crossing a first parent carrot plant with a second parent carrot plant. The resultant $F_1$ hybrid carrot root is harvested. Either the first or second parent carrot plant is the reduced pigment carrot plant produced by growing the seed which contains the gene (allelic DNA genetic factor) for reduced pigment phenotype of the present invention. A first generation ($F_1$) hybrid carrot plant is produced by growing the hybrid carrot root produced by the method of the present invention.

DETAILED DESCRIPTION OF THE INVENTION

In order to provide an understanding of some of the terms used in the specification and claims, the following definitions are provided:

α-tocopherol—as used herein, the term alpha(α)-tocopherol is synonymous with Vitamin E.

*Daucus carota*—as used herein, the term *Daucus carota* is synonymous with carrot.

Although trace levels have been speculated, no detected levels of α-tocopherol have been confirmed in *Daucus carota* until the present invention. Additionally, there are no known reports of α-tocopherol biosynthesis in any *Daucus carota* species, cultivar, in the wild or commercially available. The novel α-tocopherol biosynthesis of the present invention arose from breeding and research efforts which were conducted beginning in 1996.

The instant invention is the genetic expression of a mutant reduced pigment gene. This reduced pigment gene is associated with increased α-tocopherol biosynthesis. The genetic basis for α-tocopherol production in *Daucus carota* involves a single recessive allele. When the reduced pigment gene is incorporated into different genetic backgrounds of *Daucus carota* in the homozygous recessive condition, the α-tocopherol characteristic is transferred into these genetic backgrounds.

The seeds from the developed true-breeding reduced pigment lines can also be marketed. Reduced pigment lines can also be used as one of the parents in $F_1$ hybrid seed production resulting in an $F_1$ hybrid.

The reduced pigment gene has been designated rp. The rp gene was the result of a spontaneous mutation in the inbred line W266D. The resulting mutant was designated W266E (also called W266Erprp). The total carotenoid content in this mutation is approximately 95% less than found in other processing carrots. As discussed more fully below, analysis of this mutation led to the determination that the mutant synthesizes α tocopherol (Vitamin E) at a low rate.

Several white carrot roots were discovered during the propagation of the carrot inbred line W266D. These roots were identical in shape and size to their orange counterparts (W266D), however their roots lacked pigment. The non-pigmented roots remained pale during early growth stages and developed a slight yellow color in the phloem and outer xylem at maturity. This mutant line was called 'E-White'. The reduced pigment trait was genetically analyzed. This reduced pigment phenotype was believed to be conditioned by a single recessive gene. The symbol rp was used to describe the genetic control of this 'reduced-pigment' phenotype. Mature roots of the rprp genotype were harvested at 120 days after planting. The rprp roots exhibited a whitish-yellowish appearance and contained 141 μg carotene per gram of dry weight. In comparison, the orange-pigmented roots of W266D at the same growth stage contained almost 1800 μg carotene per gram of dry weight. Thus, it was determined that the rp gene does not completely block carotenoid synthesis since mature roots from rprp plants exhibited small amounts of β carotene.

In addition to providing a reduced pigment phenotype, the transfer of the recessive gene to different genetic backgrounds has produced the associated characteristics of increased α-tocopherol when present as a double recessive rprp. Analysis of chromatographs of extracts of the rprp roots showed a unique peak at approximately twenty-two minutes. This peak was not present in extracts of orange-rooted carrots (such as W266D) and was unlike any known carotenoid in its absorption maximum. The extracts of the rprp roots were further examined and compared to pure α-tocopherol using a high performance liquid chromatograph (HPLC) with a diode array detector. The comparison highlighted the similarity of the root peak and the α-tocopherol peak. Further chromatographic analysis was performed and large volumes of rprp root extract was prepared and injected into a liquid chromatograph. The peak at twenty-two minutes was collected in several fractions, dried, and analyzed, in comparison with a pure standard of α-tocopherol by GC-Mass Spectrometry. The data confirmed that the unique peak in the rprp extract was α-tocopherol. The production of α-tocopherol is not limited to the non-orange carrots. In the $F_1$ hybrid, the rp gene is in the heterozygous condition (RPrp). This specific hybrid has an orange carrot root and has a total carotenoid content that is generally not significantly different from the wild type (RPRP).

The mutant gene of the present invention can be easily transferred to other carrot inbreds and other genetic backgrounds by making an initial cross and selecting for the gene using standard breeding procedures. Parental lines have been developed which when crossed produce an $F_1$ hybrid which has a double recessive for the 1p gene. The α-tocopherol level in the plant and roots has ranged upwards to approximately 0.40 mg per 100 grams of fresh weight.

The present invention is directed to a carrot root with a total α-tocopherol content between about 0.01 mg per 100 grams of fresh weight of the carrot root and about 0.40 mg per 100 grams of fresh weight of the carrot root. The present invention is also directed to an $F_1$ hybrid carrot plant having a total α-tocopherol content greater than about 0.01 mg per 100 grams of fresh weight of the carrot root.

As used herein, the terms "plant" includes plant cells, plant protoplasts, plant cells of tissue culture from which carrot plants can be regenerated, plant calli, plant clumps, and plant cells that are intact in plants or parts of plants such as pollen, flowers, seeds, leaves, stems and the like. Tissue culture of carrot is described in Simon, P. W. 1985. Use and improvement of carrot for genetic studies, p. 194–198. In: M. Terzi, L. Pitto and R. Sung (eds.). Somatic embryogenesis of carrots. Consiglio Nazionale delle Richerche, Incremento Produttivita Risorse Agricole, Rome; and Simon, P. W. 1984. Carrot genetics. Plant Molecular Biology Reporter, 2:54–63, incorporated herein by reference.

EXAMPLES

The following examples are provided to further illustrate the present invention and are not intended to limit the invention beyond the limitations set forth in the appended claims.

Example 1

Several white carrot roots were discovered during the propagation of the carrot inbred line W266D. These roots were identical in shape and size to their orange counterparts (W266D), however their roots lacked pigment. The non-pigmented roots remained pale during early growth stages and developed a slight yellow color in the phloem and outer xylem at maturity. The reduced pigment carrot root that resulted from propagation of the inbred line W266E was subsequently analyzed in the $F_2$ and $BC_1$ generations in three genetic backgrounds. Initial crosses were performed using the nonpigmented carrot plant W266E as the male parent in the crosses with the orange-root inbred lines W255A, W259A, and W267A. All of these female lines had a sterile cytoplasm. Root tissue samples were taken from W266E and their hybrids using the methods described by Simon and Wolff (1987). All $F_1$ roots were orange and were harvested and then either self-pollinated or backcrossed to W266E. The $F_2$ and $BC_1$ progenies were planted and then the carrot roots were harvested and pigment content was observed.

Table 2 shows the goodness-of-fit observed in the carrot roots harvested from the $F_2$ and $BC_1$ progenies and shows the inheritance of the reduced pigment trait.

TABLE 2

| Cross | Generation | Pigmented | Reduced-Pigment | Expected Ratio | $x^2$ | p |
|---|---|---|---|---|---|---|
| W255A × W266E | $F_2$ | 123 | 42 | 124:41 | 0.032 | .98 |
| W259A × W266E | $F_2$ | 134 | 49 | 138:45 | 0.470 | .55 |
| W267A × W266E | $F_2$ | 175 | 53 | 175:53 | 0.370 | .63 |
| [W266E × (W259A × W266E)] | $BC_1$ | 161 | 132 | 146:146 | 2.880 | .10 |
| [W266E × (W255A × W266E)] | $BC_1$ | 138 | 142 | 140:140 | 0.057 | .97 |
| [W266E × (W267A × W266E) | $BC_1$ | 150 | 131 | 140:140 | 1.290 | .27 |

These results indicate that the reduced pigment phenotype is conditioned by a single recessive gene.

Example 2

Table 3 shows the amounts of carotenoid and a tocopherol present in various genotypes. The inbred line W266E has approximately 0.27 mg of α-tocopherol equivalents per 100 grams of fresh weight of the carrot. This inbred line is a standard inbred line of processing carrot carrying the reduced pigment (rp) mutation in the homozygous recessive condition. Alpha-tocopherol was not found in the W266DRPRP inbred line which is a standard inbred line of processing carrot. In addition, α-tocopherol was not present in the $F_1$ hybrid from the cross of W266E, which was used as the female parent, with W297B, an unreleased inbred line of processing carrot which was used as the male parent.

TABLE 3

| Genotype | mg total carotenoid[1] per 100 g fresh weight | mg α-tocopherol equivalents[2] per 100 g fresh weight |
|---|---|---|
| W266DRPRP (Inbred Line) | 17.4 ± 0.26 | 0.00 |
| W266E (Inbred Line) | 1.4 ± 0.23 | 0.27 ± 0.05 |
| W266E × W279B (F1 Hybrid) | 17.3 ± 0.62 | 0.00 |
| Asgrow Hybrid[3] 1 | — | 0.0 |
| Asgrow Hybrid[3] 2 | — | 0.0 |
| Asgrow Hybrid[3] 3 | — | 0.0 |

[1]Carotenoids were measured using spectrophotometry according to the method of P. Simon and X. Wolff, 1987, Journal of Agricultural and Food Chemistry, 35:1017–1022.
[2]Alpha tocopherol equivalents are a standard measure of Vitamin E. One α tocopherol equivalent is equal to one mg of α tocopherol. Tocopherol was measured using a modification of the method reported by S. R. Norris, T. R. Barette, and D. DellaPenna, 1995, Plant Cell, 7:2139–2149.
[3]Obtained from Dr. Larry Baker of Asgrow/Seminis of DeForest, Wisconsin.

DEPOSIT INFORMATION

*Daucus carota* seeds have been placed on deposit with the American Type Culture Collection (ATTC), Manassas, Va. 20110, under Deposit Accession Number 203147 on Aug. 19, 1998.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A carrot seed containing two recessive alleles, each designated rp, wherein a representative sample of the seed has been deposited under ATCC Accession No. 203147.

2. A reduced pigment carrot plant produced by growing the seed of claim 1.

3. Pollen of the plant of claim 2.

4. An ovule of the plant of claim 2.

5. A tissue culture comprising regenerable cells of the plant of claim 2, wherein said plant comprises two rp allels.

6. A carrot plant regenerated from tissue culture of claim 5, wherein said carrot plant has all of the physiological and morphological characteristics of the plant from which the tissue culture was derived.

7. A method for producing $F_1$ hybrid carrot root comprising crossing a first parent carrot plant with a second parent carrot plant and harvesting the resultant $F_1$ hybrid carrot root wherein said first or second parent carrot plant is the carrot plant of claim 2, and wherein said $F_1$ hybrid carrot root comprises at least one rp allele.

8. A method for producing $F_1$ hybrid carrot root comprising crossing a first parent carrot plant with a second parent carrot plant and harvesting the resultant $F_1$ hybrid carrot root, wherein said first or second parent carrot plant is the carrot carrot plant of claim 2 and is the female parent plant and wherein said $F_1$ hybrid carrot root comprises at least one rp allele.

9. A first generation ($F_1$) hybrid carrot plant produced by growing said $F_1$ hybrid carrot root produced by the method of claim 7.

10. An inbred carrot seed designated W266E having ATCC Accession No. 203147.

11. A plant or its parts produced by growing the seed of claim 10.

12. Pollen of the plant of claim 11.

13. An ovule of the plant of claim 11.

14. A carrot plant having all of the physiological and morphological characteristics of the plant of claim 11.

15. Tissue culture of the plant of claim 11.

16. A method for producing a hybrid carrot seed comprising crossing an inbred plant according to claim 11 with another, different carrot plant.

17. A hybrid seed produced by the method of claim 16, wherein said hybrid seed comprises at least one rp allele.

18. A hybrid plant or its parts produced by growing said hybrid carrot seed of claim 17.

19. Seed produced from said hybrid plant of claim 18, wherein said seed comprises at least one rp allele.

20. A method for producing $F_1$ hybrid carrot seed comprising crossing a first inbred parent carrot plant with a second inbred parent carrot plant and harvesting the resultant $F_1$ hybrid carrot seed wherein said first or second inbred parent carrot plant is the carrot plant of claim 11, and wherein said $F_1$ hybrid carrot seed comprises at least one rp allele.

21. A hybrid seed produced by the method of claim 20.

22. A hybrid plant or its parts produced by growing said hybrid carrot seed of claim 21.

23. Seed produced from said hybrid plant of claim 22, wherein said seed comprises at least one rp allele.

24. A method for producing a carrot variety designated W266E-derived carrot plant having at least one rp allele comprising:

a) crossing carrot variety W266E, representative seed of said variety having been deposited under ATCC Accession No. 203147, with a second carrot plant to yield progeny carrot seed; and b) growing said progeny seed, under plant growth conditions, to yield said carrot variety W266E-derived carrot plant.

25. The method of claim 24, further comprising:

c) crossing said carrot variety W266E-derived carrot plant with itself or another carrot plant to yield additional carrot variety W266E-derived progeny carrot seed;

d) growing said progeny carrot seed of step (c) under plant growth conditions, to yield additional carrot variety W266E-derived carrot plants;

e) repeating the crossing and growing steps of (c) and (d) from 0 to 7 times to generate further carrot variety W266E-derived carrot plants; and f) selecting plants from step (e) having at least one rp allelel.

\* \* \* \* \*